United States Patent
Borgmeier et al.

(10) Patent No.: US 7,026,506 B2
(45) Date of Patent: Apr. 11, 2006

(54) METHOD FOR PRODUCING ACRYLIC ACID BY HETEROGENEOUSLY CATALYZED GAS-PHASE OXIDATION OF PROPENE WITH MOLECULAR OXYGEN IN A REACTION ZONE

(75) Inventors: Frieder Borgmeier, Mannheim (DE); Jochen Petzoldt, Mannheim (DE); Hartmut Hibst, Schriesheim (DE); Andreas Tenten, Maikammer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 90 days.

(21) Appl. No.: 10/474,202

(22) PCT Filed: Apr. 12, 2002

(86) PCT No.: PCT/EP02/04073

§ 371 (c)(1),
(2), (4) Date: Oct. 17, 2003

(87) PCT Pub. No.: WO02/083615

PCT Pub. Date: Oct. 24, 2002

(65) Prior Publication Data

US 2004/0082810 A1  Apr. 29, 2004

(30) Foreign Application Priority Data

Apr. 17, 2001 (DE) .......................................... 101 18 814

(51) Int. Cl.
*C07C 51/16* (2006.01)

(52) U.S. Cl. ......................... 562/547; 562/545; 562/598
(58) Field of Classification Search ................. 560/512, 560/598; 502/300, 353
See application file for complete search history.

(56) References Cited

U.S. PATENT DOCUMENTS

| 5,380,933 | A | * | 1/1995 | Ushikubo et al. | ............ 562/549 |
| 6,180,825 | B1 | * | 1/2001 | Lin et al. | ..................... 562/549 |
| 6,525,217 | B1 | * | 2/2003 | Unverricht et al. | ......... 562/544 |
| 6,653,253 | B1 | * | 11/2003 | Lin | ............................ 502/113 |
| 2003/0187299 | A1 | * | 10/2003 | Machhammer et al. | ..... 562/547 |

FOREIGN PATENT DOCUMENTS

| DE | 198 35 247 | 2/1999 |
| DE | 100 29 338 | 1/2002 |
| DE | 100 33 121 | 1/2002 |
| DE | 100 46 672 | 3/2002 |
| EP | 0 529 853 | 3/1993 |
| EP | 0 608 838 | 8/1994 |
| EP | 0 767 164 | 4/1997 |
| EP | 0 895 809 | 2/1999 |
| EP | 0 962 253 | 12/1999 |
| EP | 1 090 684 | 4/2001 |

(Continued)

OTHER PUBLICATIONS

G. Centi et al., ed. Proceedings ISO'99 Rimini (Italy), pp. 143–144 Sep. 10–11, 1999.
Catalysis Today, vol. 49, pp. 141–153 1999.
Applied Catalysis A: General, vol. 194–195, pp. 479–485 2000.
Kinetics and Catalysis, vol. 40, No. 3, pp. 401–404 1999.

*Primary Examiner*—Johann Richter
*Assistant Examiner*—Karl Puttlitz
(74) *Attorney, Agent, or Firm*—Oblon, Spivak, McClelland, Maier & Neustadt, P.C.

(57) ABSTRACT

In a process for the preparation of acrylic acid by heterogeneously catalyzed gas-phase oxidation of propene with molecular oxygen in a reaction zone, the catalytically active material is a multimetal oxide which contains the elements Mo, V, Te and/or Sb and has a specific structure.

19 Claims, 5 Drawing Sheets

FOREIGN PATENT DOCUMENTS

| | | |
|---|---|---|
| JP | 7-53448 | 2/1995 |
| JP | 7-232071 | 9/1995 |
| JP | 8-57319 | 3/1996 |
| JP | 10-28862 | 2/1998 |
| JP | 10-36311 | 3/1998 |
| JP | 10-57813 | 3/1998 |
| JP | 10-310539 | 11/1998 |
| JP | 10-330343 | 12/1998 |
| JP | 11-42434 | 2/1999 |
| JP | 11-43314 | 2/1999 |
| JP | 11-57479 | 2/1999 |
| JP | 11-169716 | 6/1999 |
| JP | 11-263745 | 9/1999 |
| JP | 11-285637 | 10/1999 |
| JP | 11285637 | * 10/1999 |
| JP | 11-343261 | 12/1999 |
| JP | 11-343262 | 12/1999 |
| JP | 2000-37623 | 2/2000 |
| JP | 2000-51693 | 2/2000 |
| WO | 99/03825 | 1/1999 |
| WO | 00/29105 | 5/2000 |
| WO | 00/29106 | 5/2000 |
| WO | 02 06199 | 1/2002 |

* cited by examiner

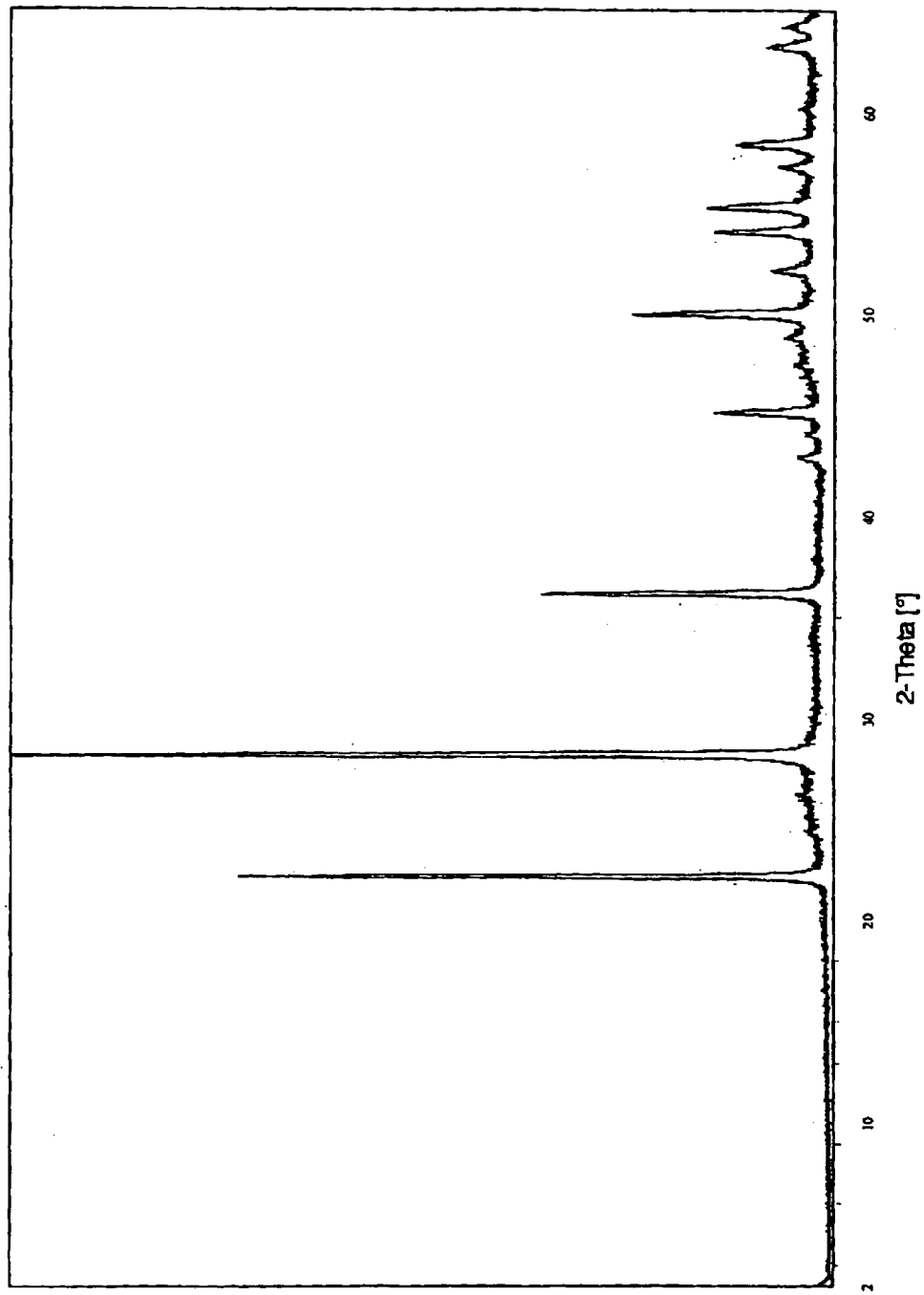

METHOD FOR PRODUCING ACRYLIC ACID BY HETEROGENEOUSLY CATALYZED GAS-PHASE OXIDATION OF PROPENE WITH MOLECULAR OXYGEN IN A REACTION ZONE

BACKGROUND OF THE INVENTION

1. Field of the Invention

The present invention relates to a process for the preparation of acrylic acid by heterogeneously catalyzed gas-phase oxidation of propene with molecular oxygen over at least one multimetal oxide active material present in a reaction zone A and having the stoichiometry I $$Mo_1V_bM_c^1M_d^2O_n \qquad (I),$$

where
$M^1$ is Te and/or Sb,
$M^2$ is at least one of the elements from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In,
b is from 0.01 to 1,
c is from >0 to 1, preferably from 0.01 to 1,
d is from >0 to 1, preferably from 0.01 to 1, and
n is a number which is determined by the valency and frequency of the elements other than oxygen in (I).

2. Description of the Background

Multimetal oxide active materials which have a stoichiometry corresponding to the formula (I) are known (cf. for example EP-A 608838, EP-A 529 853, JP-A 7-232 071, JP-A 10-57813, JP-A 2000-37623, JP-A 10-36311, WO 00/29105, Proceedings ISO'99, Rimini (Italy), Sept. 10–11, 1999, G. Centi and S. Perathoner Ed., SCI Pub. 1999, EP-A 767 164, Catalysis Today 49 (1999), pages 141–153, EP-A 962 253, Applied Catalysis A: General 194 to 195 (2000), pages 479 to 485, JP-A 11/169716, EP-A 895 809, DE-A 19835247, DE-A 10 029 338, JP-A 8-57319, JP-A 10-28862, JP-A 11-43314, JP-A 11-57479, WO 00/29106, JP-A 10-330343, JP-A 11-285637, JP-A 10-310539, JP-A 11-42434, JP-A 11-343261, JP-A 11-343262, WO-99/03825, JP-A 7-53448, JP-A 2000-51693, JP-A 11-263745 and the prior application DE-A 10046672.

In the prior art cited, the multimetal oxide active materials (I) were primarily recommended as catalysts for the heterogeneously catalyzed gas-phase oxidation and/or gas-phase ammoxidation of saturated hydrocarbons to α,β-ethylenically unsaturated carboxylic acids and/or their nitriles (e.g. propane→acrylic acid).

The prior art considered also discloses that multimetal oxide active materials having the stoichiometry (I) occur in the form of two crystalline phases which differ from one another and frequently referred to as the i-phase and the k-phase (cf. for example JP-A 11-43314, DE-A 19835247 and DE-A 10046672). Very recent investigations have led to the discovery that the X-ray diffraction pattern of both phases has the reflection of strongest intensity at the peak position 2θ=22.2±0.4°. Moreover, the X-ray diffraction pattern of the i-phase, in contrast to the k-phase, contains no reflection with the peak position 2θ=27.3±0.4°, whereas the X-ray diffraction pattern of the k-phase, in contrast to the i-phase, contains no reflection with the peak position 2θ=50.0±0.3°. Both phases additionally have a reflection with the peak position 2θ=28.2±0.4°. JP-A 11-343262 and JP-A 11-343261 recommend multimetal oxide active materials (I) which have the structure of the k-phase as catalysts for the heterogeneously catalyzed gas-phase oxidation of acrolein with molecular oxygen to acrylic acid.

JP-A 7-53448 recommends multimetal oxide active materials having the stoichiometry (I) very generally as active materials suitable for a process for the preparation of acrylic acid by heterogeneously catalyzed gas-phase oxidation of propene with molecular oxygen over catalysts present in a reaction zone. The propene to be oxidized may also contain certain proportions of propane. According to JP-A 7-53448, preferred multimetal oxide active materials (I) are those which have the structure of the k-phase. They are also used in the examples of JP-A 7-53448. However, the disadvantage of these multimetal oxide active materials is that their activity with respect to a gas-phase catalytic oxidation of propene to acrylic acid in a reaction zone is unsatisfactory. Similarly, the multimetal oxide active materials having the stoichiometry (I) of EP-A-1090684 are also not completely satisfactory for a propene oxidation.

WO 00/29105 recommends multimetal oxide active materials having the stoichiometry (I) inter alia also as catalysts for a gas-phase catalytic oxidation of $C_2$— to $C_8$-alkenes. WO 00/29105 also considers propane/propene mixtures as possible raw materials. According to WO 00/29105, multimetal oxide active materials having the stoichiometry (I) are however not very suitable for the abovementioned purpose when they have a crystalline structure whose X-ray diffraction pattern consists of reflections having small half-widths. Rather, according to WO 00/29105, only those multimetal oxide active materials having the stoichiometry (I) which lack short-range order possess satisfactory catalytic activity.

The general usability of multimetal oxide active materials having the stoichiometry (I) as catalysts for the heterogeneously catalyzed gas-phase oxidation of olefins with molecular oxygen is also discussed in WO 99/03825, JP-A 11-42434, JP-A 10-310539, JP-A 11-57479 and JP-A 10-28862. In none of the examples, however, is an olefin oxidation mentioned.

JP-A 8-57319 discloses that Mo and/or V-containing multimetal oxide active materials can be activated by treatment with acid.

SUMMARY OF THE INVENTION

It is an object of the present invention to provide a process for the preparation of acrylic acid by heterogeneously catalyzed gas-phase oxidation of propene with molecular oxygen over at least one multimetal oxide active material present in a reaction zone A and having the stoichiometry (I), which process, on the one hand, has a selectivity of the acrylic acid formation which roughly corresponds to that of JP-A 7-53448 with the use of multimetal oxide active materials (I) having the k-phase structure, but which, on the other hand, uses multimetal oxide active materials (I) having substantially higher activity.

We have found that this object is achieved by a process for the preparation of acrylic acid by heterogeneously catalyzed gas-phase oxidation of propene with molecular oxygen over at least one multimetal oxide active material present in a reaction zone A and having the stoichiometry (I), wherein the X-ray diffraction pattern of the at least one multimetal oxide active material (I) has reflections h, i and k whose peaks are at the diffraction angles (2θ) 22.2±0.4° (h), 27.3±0.4° (i) and 28.2±0.4° (k), the reflection h being the one with the strongest intensity within the X-ray diffraction pattern and having a half-width of not more than 0.5°,
the intensity $P_i$ of the reflection i and the intensity $P_k$ of the reflection k fulfilling the relationship 0.65≦R≦0.85, where R is the intensity ratio defined by the formula $$R = P_i/(P_i + P_k)$$

and the half-width of the reflection i and that of the reflection k are each ≦1°.

BRIEF DESCRIPTION OF THE DRAWiNGS

FIG. 5 is the X-ray diffraction pattern of multimetal oxide comparison catalyst of Example (Sd).

DETAILED DESCRIPTION OF THE PREFERRED EMBODIMENTS

Figure 1:
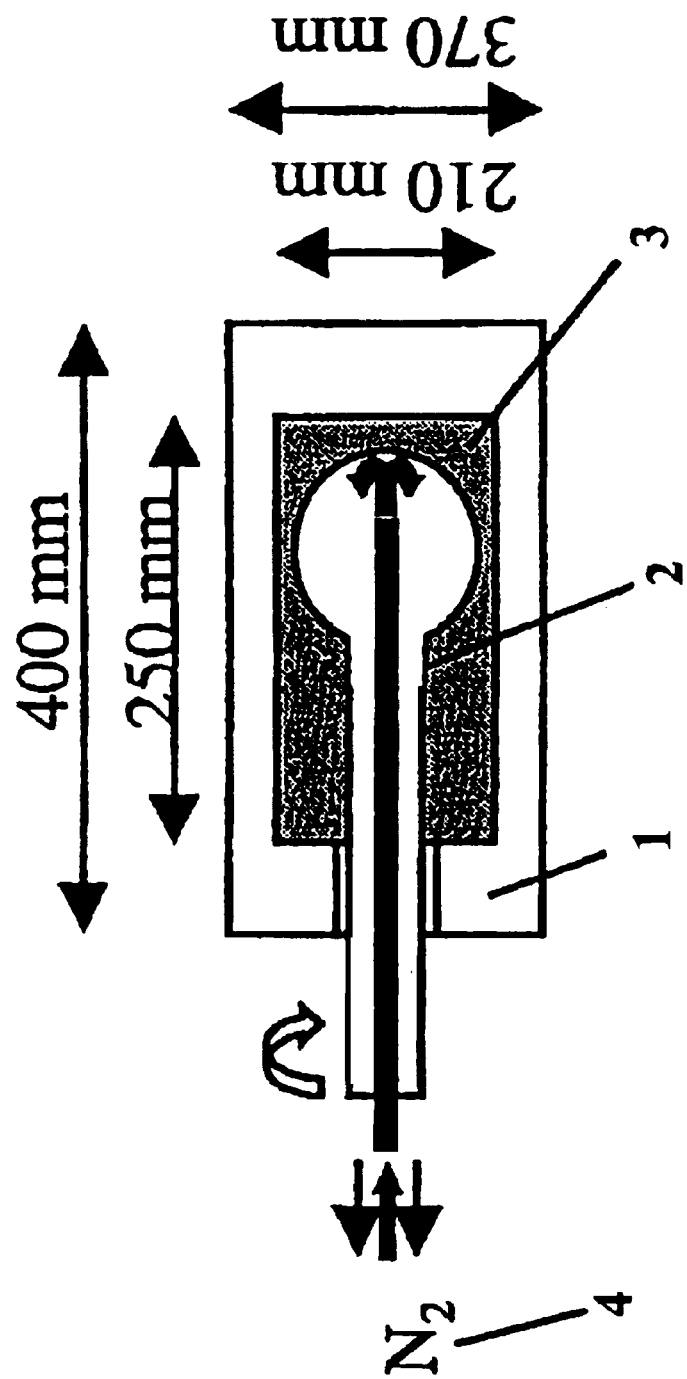
FIG. 1 is a schematic diagram of a rotary sphere oven.

This means that the multimetal oxide active materials (I) to be used according to the invention must contain a significant proportion of i-phase. As a rule, the proportion of the i-phase in the novel process is at least 75% by weight, based on the weight of the multimetal oxide active material (I) to be used. Accordingly, novel processes include those in which the proportion of the i-phase, based on the weight of the multimetal oxide active material (I) to be used according to the invention, is at least 80 or at least 85 or at least 90 or at least 95% by weight. Multimetal oxide active materials (I) which consist exclusively of i-phase are preferably used for the novel process.

A specific measure for the proportion of i-phase in a multimetal oxide active material (I) is the intensity ratio R. According to the invention, 0.67≦R≦0.75 and very particularly preferably R=from 0.70 to 0.75 or R=0.72.

The use of multimetal oxide active materials (I) in which $M^1$ is Te is preferred according to the invention. Furthermore, those multimetal oxide active materials (I) in which $M^2$ is Nb, Ta, W and/or titanium are advantageous for the novel process. Preferably, $M^2$ is Nb. The stoichiometric coefficient b of the multimetal oxide active materials (I) to be used according to the invention is advantageously from 0.1 to 0.6. In a corresponding manner, the preferred range for the stoichiometric coefficient c is from 0.01 to 1 or from 0.05 to 0.4 and advantageous values for d are from 0.01 to 1 or from 0.1 to 0.6. Particularly advantageous multimetal oxide active materials (I) to be used according to the invention are those in which the stoichiometric coefficients b, c and d are simultaneously in the abovementioned preferred ranges. Further stoichiometries suitable according to the invention are those which are disclosed in the publications of the prior art cited at the outset, in particular in JP-A 7-53448.

A specific process for the preparation of multimetal oxide active materials (I) to be used according to the invention, in which materials the proportion of i-phase is dominant, is disclosed, for example, in JP-A 11-43314 and the prior application DE-A 10046672, in which the relevant multimetal oxide active materials (I) are recommended as catalysts for the heterogeneously catalyzed oxydehydrogenation of ethane to ethylene and as catalysts for the heterogeneously catalyzed gas-phase oxidation of propane to acrylic acid.

Accordingly, a multimetal oxide active material having the stoichiometry (I), which is a mixture of i-phase and other phases (e.g. k-phase), is first produced in a manner known per se and disclosed in most of the cited publications of the prior art (for example, also as described in the prior application DE-A 10033121). In this mixture, the proportion of i-phase can now be increased, for example, by removing the other phases, for example the k-phase, under the microscope or washing the multimetal oxide active material with suitable liquids. Examples of suitable such liquids are aqueous solutions of organic acids (e.g. oxalic acid, formic acid, acetic acid, citric acid and tartaric acid), inorganic acids (e.g. nitric acid), alcohols and aqueous hydrogen peroxide solutions. Furthermore, JP-A 7-232071 also discloses a process for the preparation of multimetal oxide active materials (I) to be used according to the invention.

In a less systematic manner, multimetal oxide active materials (I) to be used according to the invention are obtainable by the preparation method published in DE-A 19835247. According to this, a very intimate, preferably finely divided, dry blend is produced from suitable sources of their elemental constituents and this blend is treated thermally at from 350 to 700° C. or from 400 to 650° C. of from 400 to 600° C. The thermal treatment can be carried out in principle under an oxidizing, reducing or inert atmosphere. A suitable oxidizing atmosphere is, for example, air, air enriched with molecular oxygen or air depleted in oxygen. Preferably, the thermal treatment is carried out under an inert atmosphere, for example under molecular nitrogen and/or noble gas. Usually, the thermal treatment is effected at atmospheric pressure (1 atm). Of course, the thermal treatment can also be effected under reduced or under superatmospheric pressure.

If the thermal treatment is effected under a gaseous atmosphere, this may be either stationary or flowing. Altogether, the thermal treatment may take up to 24 hours or more.

The thermal treatment is preferably first carried out under an oxidizing (oxygen-containing) atmosphere (e.g. under air) at from 150 to 400° C. or from 250 to 350° C. Thereafter, the thermal treatment is expediently continued under inert gas at from 350 to 700° C. or from 400 to 650° C. or from 400 to 600° C. Of course, the thermal treatment can also be carried out in such a way that the catalyst precursor material is first tableted before its thermal treatment (if required after being powdered and if necessary with addition of from 0.5 to 2% by weight of finely divided graphite), is then subjected to a thermal treatment and is subsequently converted into chips again.

The thorough mixing of the starting compounds in the preparation of multimetal oxide active materials (I) to be used according to the invention can be carried out in dry or in wet form. If it is effected in dry form, the starting compounds are expediently used in the form of finely divided powder and, after mixing and any compaction, are subjected to the calcination (thermal treatment).

Preferably, however, the thorough mixing is effected in wet form. Usually, the starting compounds are mixed with one another in the form of an aqueous solution and/or suspension. The aqueous material is then dried and is calcined after drying. The aqueous material is expediently an aqueous solution or an aqueous suspension. The drying process is preferably carried out immediately after preparation of the aqueous mixture and by spray-drying (the outlet temperatures are as a rule from 100 to 150° C.; the spray-drying can be carried out by the cocurrent or countercurrent method), which requires a particularly intimate dry blend, especially when the aqueous material to be spray-dried is an aqueous solution.

Suitable sources of the elemental constituents for carrying out the above-described method of preparation of the multimetal oxide active materials (I) to be used according to the invention are all those which are capable of forming oxides and/or hydroxides on heating (if necessary in air). Of course, oxides and/or hydroxides of the elemental constituents may also be concomitantly used or exclusively used as such starting compounds.

Sources of the element Mo which are suitable according to the invention are, for example, molybdenum oxides, such as molybdenum trioxide, molybdates, such as ammonium heptamolybdate tetrahydrate, and molybdenum halides, such as molybdenum chloride.

Suitable starting compounds of the element V which are to be concomitantly used according to the invention are, for example, vanadyl acetylacetonate, vanadates, such as ammonium metavanadate, vanadium oxides, such as vanadium pentoxide ($V_2O_5$), vanadium halides, such as vanadium tetrachloride ($VCl_4$), and vanadium oxyhalides, such as $VOCl_3$. Other vanadium starting compounds which may be concomitantly used are also those which contain the vanadium in oxidation state +4.

Suitable sources of the element tellurium are, according to the invention, tellurium oxides, such as tellurium dioxide, metallic tellurium, tellurium halides, such as $TeCl_2$, and also telluric acids, such as orthotelluric acid $H_6TeO_6$.

Advantageous antimony starting compounds are antimony halides, such as $SbCl_3$, antimony oxides, such as antimony trioxide ($Sb_2O_3$), antimonic acids, such as HSb$(OH)_6$, and also antimony oxide salts, such as antimony oxide sulfate $(SbO)_2SO_4$.

Niobium sources which are suitable according to the invention are, for example, niobium oxides, such as niobium pentoxide ($Nb_2O_5$), niobium oxyhalides, such as $NbOCl_3$, niobium halides, such as $NbCl_5$, and also complex compounds of niobium and organic carboxylic acids and/or dicarboxylic acids, e.g. oxalates and alcoholates. Of course, the Nb-containing solutions used in EP-A 895 809 are also suitable as a niobium source.

Regarding all other possible elements $M^2$, starting compounds which are particularly suitable according to the invention are their halides, nitrates, formates, oxalates, acetates, carbonates and/or hydroxides. Suitable starting compounds are often also their oxo compounds, for example tungstates, or the acids derived from these. Frequently, ammonium salts are also used as starting compounds.

Other suitable starting compounds for the preparation of the novel multimetal oxide active materials (I) are polyanions of the Anderson type, as described, for example, in Polyhedron Vol. 6, No. 2, pages 213–218, 1987. A further suitable literature source for polyanions of the Anderson type is Kinetics and Catalysis, Vol. 40, No. 3, 1999, pages 401 to 404.

Other polyanions suitable as starting compounds are, for example, those of the Dawson or Keggin type. Starting compounds which are preferably used according to the invention are those which are converted at elevated temperatures into their oxides, either in the presence or in the absence of oxygen, possibly with liberation of gaseous compounds.

The multimetal oxide active materials (I) obtainable as described and to be used according to the invention can be used for the novel process as such for example as powder or after tableting of the powder (frequently with addition of from 0.5 to 2% by weight of finely divided graphite) and subsequent comminution to give chips or in the form of moldings. The catalyst bed may be a fixed bed, a moving bed or a fluidized bed.

The formation to moldings can be effected, for example, by application to a support, as described in prior application DE-A 10051419.

The supports to be used for multimetal oxide active materials (I) to be employed according to the invention are preferably chemically inert, i.e. they do not substantially intervene in the course of the catalytic gas-phase oxidation of propene to acrylic acid which is catalyzed by the multimetal oxide active materials to be used according to the invention.

According to the invention, particularly suitable materials for the supports comprises alumina, silica, silicates, such as clay, kaolin, steatite, pumice, aluminum silicate and magnesium silicate, silicon carbide, zirconium dioxide and thorium dioxide.

The surface of the support may be either smooth or rough. Advantageously, the surface of the support is rough since pronounced surface roughness generally results in increased adhesive strength of the applied active material coat.

Frequently, the surface roughness $R_z$ of the support is from 5 to 200 µm, often from 20 to 100 µm (determined according to DIN 4768, Sheet 1, using a Hommel tester for DIN-ISO measured surface variables, from Hommelwerke, Germany).

Furthermore, the support material may be porous or nonporous. The support material is expediently nonporous (total volume of the pores<1% by volume, based on the volume of the support).

The thickness of the active oxide material coat present on the novel coated catalyst is usually from 10 to 1 000 µm. However, it may also be from 50 to 700 µm, from 100 to 600 µm or from 150 to 400 µm. Possible coat thicknesses are also from 10 to 500 µm, from 100 to 500 µm or from 150 to 300 µm.

In principle, any desired geometries of the supports are suitable for the novel process. Their longest dimension is as a rule from 1 to 10 mm. However, spheres or cylinders, in particular hollow cylinders, are preferably used as supports. Advantageous diameters for spherical supports are from 1.5 to 4 mm. If cylinders are used as supports, their length is preferably from 2 to 10 mm and their external diameter is preferably from 4 to 10 mm. In the case of rings, the wall thickness is moreover usually from 1 to 4 mm. Annular supports suitable according to the invention may also have a length of from 3 to 6 mm, an external diameter of from 4 to 8 mm and a wall thickness of from 1 to 2 mm. However, a support ring geometry of 7 mm×3 mm×4 mm or of 5 mm×3 mm×2 mm (external diameter×length×internal diameter) is also possible.

The coated catalysts to be used according to the invention can be most simply prepared by preforming active oxide materials of the formula (I), converting them into a finely divided form and finally applying them to the surface of the support with the aid of a liquid binder. For this purpose, the surface of the support is most simply moistened with a liquid binder and a coat of the active material is bound to the moistened surface by bringing said support into contact with finely divided active oxide material of the formula (I). The coated support is then dried. Of course, the process can be repeated periodically for obtaining a greater coat thickness. In this case, the coated parent body becomes the new support, etc.

The fineness of the catalytically active oxide material of the formula (I) which is to be applied to the surface of the support is of course adapted to the desired coat thickness. With a coat thickness range from 100 to 500 µm, for example, those active material powders of which at least 50% with a total number of powder particles pass through a sieve having a mesh size of from 1 to 20 µm and whose numerical proportion of particles having a maximum dimension above 50 µm is less than 10% are suitable. As a rule, the distribution of the maximum dimensions of the powder particles corresponds to a Gaussian distribution, as a result of the preparations. Frequently, the particle size distribution is as follows:

| D (µm) | 1 | 1.5 | 2 | 3 | 4 | 6 | 8 | 12 | 16 | 24 | 32 | 48 | 64 | 96 | 128 |
|---|---|---|---|---|---|---|---|---|---|---|---|---|---|---|---|
| x | 80.5 | 76.3 | 67.1 | 53.4 | 41.6 | 31.7 | 23 | 13.1 | 10.8 | 7.7 | 4 | 2.1 | 2 | 0 | 0 |
| y | 19.5 | 23.7 | 32.9 | 46.6 | 58.4 | 68.3 | 77 | 86.9 | 89.2 | 92.3 | 96 | 97.9 | 98 | 100 | 100 |

Here, the meanings are as follows:
D is the diameter of the particle,
x is the percentage of particles whose diameter is $\geq D$ and
y is the percentage of particles whose diameter is <D.

For carrying out the coating process described on an industrial scale, it is advisable, for example, to use the process principle disclosed in DE-A 2909671 and that disclosed in DE-A 10051419. This means that the supports to be coated are initially taken in a preferably inclined (the angle of inclination is as a rule $\geq 0°$ and $\leq 90°$, generally $\geq 30°$ and $\leq 90°$; the angle of inclination is the angle of the central axis of the rotating container relative to the horizontal) rotating container (for example rotating pan or coating drum). The rotating container passes the supports, which are, for example, spherical or cylindrical, under two metering apparatuses arranged successively a distance apart. The first of the two metering apparatuses expediently corresponds to a nozzle (for example an atomizer nozzle operated with compressed air) through which the supports rolling in the rotating pan are sprayed with the liquid binder and are moistened in a controlled manner. The second metering apparatus is present outside the atomization cone of the liquid binder sprayed in and serves for feeding in the finely divided oxidic active material (for example via a shaking conveyor or a powder screw). The spherical supports moistened in a controlled manner take up the supplied active material powder, which, owing to the rolling movement, becomes compacted on the outer surface of the, for example, cylindrical or spherical support to form a cohesive coat.

If required, the support provided with a base coat in this manner passes through the spray nozzles again in the course of the subsequent revolution, is moistened thereby in a controlled manner in order to be able to take up a further coat of finely divided oxidic active material in the course of the further movement, etc. (intermediate drying is as a rule not necessary). Finely divided oxidic active material and liquid binder are fed in as a rule continuously and simultaneously.

The liquid binder can be removed after the end of the coating, for example by the action of hot gases, such as $N_2$ or air. It is noteworthy that the coating process described results in completely satisfactory adhesion of the successive coats to one another as well as of the base coat to the surface of the support.

What is important for the coating method described above is that the moistening of the support surface to be coated is carried out in a controlled manner. In short, this means that the support surface is expediently moistened in such a way that, although it has adsorbed liquid binder, no liquid phase as such appears visually on the support surface. If the support surface is too moist, the finely divided catalytically active oxide material agglomerates to form separate agglomerates instead of being attracted to the surface. Detailed information in this context can be found in DE-A 2909671 and DE-A 10051419.

The abovementioned final removal of the liquid binder used can be carried out in a controlled manner, for example by evaporation and/or sublimation. In the simplest case, this can be effected by the action of hot gases of corresponding temperature (frequently from 50 to 300° C., often 150° C.). However, it is only possible to effect preliminary drying by means of the action of hot gases. The final drying can then be carried out, for example, in a drying oven of any desired type (for example a belt drier) or in the reactor. The temperature acting should not be above the calcination temperature used for the preparation of the oxidic active material. Of course, the drying can also be carried out exclusively in a drying oven.

Regardless of the type and of the geometry of the support, the following can be used as binders for the coating process: water, monohydric alcohols, such as ethanol, methanol, propanol and butanol, polyhydric alcohols, such as ethylene glycol, 1,4-butanediol, 1,6-hexanediol or glycerol, monobasic or polybasic organic carboxylic acids, such as propionic acid, oxalic acid, malonic acid, glutaric acid or maleic acid, amino alcohols, such as ethanolamine or diethanolamine, and monofunctional or polyfunctional organic amides, such as formamide. Other advantageous binders are solutions consisting of from 20 to 90% by weight of water and from 10 to 80% by weight of an organic compound which is dissolved in water and whose boiling point or sublimation temperature at atmospheric pressure (1 atm) is >100° C., preferably >150° C. Advantageously, the organic compound is selected from the above list of possible organic binders. The organic fraction of the abovementioned aqueous binder solutions is preferably from 10 to 50, particularly preferably from 20 to 30, % by weight. Other suitable organic components are monosaccharides and oligosaccharides, such as glucose, fructose, sucrose or lactose, and polyethylene oxides and polyacrylates.

What is important is that the preparation of coated catalysts suitable according to the invention can be carried out not only by application of the prepared, finely divided active oxide materials of the formula (I) to the moistened support surface.

Rather, instead of the active oxide material, a finely divided precursor material thereof can also be applied to the moistened support surface (using the same coating process and binder) and the calcination can be carried out after drying of the coated support.

A suitable finely divided precursor material of this type is, for example, that material which is obtainable by first producing a very intimate, preferably finely divided, dry blend from the sources of the elemental constituents of the desired active oxide material of the formula (I) (for example by spray-drying an aqueous suspension or solution of the sources) and subjecting this finely divided dry blend (if necessary after tabletting with addition of from 0.5 to 2% by weight of finely divided graphite) to a thermal treatment at from 150 to 350° C., preferably at from 250 to 350° C., under an oxidizing (oxygen-containing) atmosphere (e.g. under air) for a few hours and finally, if required, milling said dry blend.

After the coating of the supports with the precursor material, calcination is then effected, preferably under inert gas atmosphere (all other atmospheres are also suitable) at from 360 to 700° C. or from 400 to 650° C. or from 400 to 600° C.

Of course, the shaping of multimetal oxide active materials (I) which can be used according to the invention can also be carried out by extrusion and/or tabletting of both finely divided multimetal oxide active material (I) and finely divided precursor material of a multimetal oxide active material (I).

Suitable geometries are spheres, solid cylinders and hollow cylinders (rings). The maximum dimension of the above-mentioned geometries is as a rule from 1 to 10 mm. In the case of cylinders, their length is preferably from 2 to 10 mm and their external diameter is preferably from 4 to 10 mm. In the case of rings, the wall thickness is moreover usually from 1 to 4 mm. Annular unsupported catalysts suitable according to the invention can also have a length of from 3 to 6 mm, an external diameter of from 4 to 8 mm and a wall thickness of from 1 to 2 mm. However, an unsupported catalyst ring may also have a geometry of 7 mm×3 mm×4 mm or of 5 mm×3 mm×2 mm (external diameter× length×internal diameter).

Of course, all those geometries of DE-A 10101695 are also suitable for the geometry of the multimetal oxide active materials (I) to be used for the novel process.

It is important according to the invention that the multimetal oxide active materials (I) to be used according to the invention have an X-ray diffraction pattern (in this document, always based on Cu-K$_\alpha$ radiation) which includes reflections h, i and k, whose peaks are at the diffraction angles (2θ) 22.2±0.45 (h), 27.3±0.45 (i) and 28.2±0.45 (k), the reflection h having the strongest intensity within the X-ray diffraction pattern and having a half-width of not more than 0.5°, the intensity $P_i$ of the reflection i and the intensity $P_k$ of the reflection k fulfilling the relationship 0.65≦R≦0.85, where R is the intensity ratio defined by the formula $$R=P_i/(P_i+P_k)$$

and the half-width of the reflection i and that of the reflection k are each ≦1°.

The definition of the intensity of a reflection in the X-ray diffraction pattern is based in this document on the definition set out in DE-A 19835247 and that set out in DE-A 10051419 and DE-A 10046672.

This means that if $A^1$ is the peak of a reflection 1 and $B^1$ is the nearest pronounced minimum (minima having shoulders are not taken into account) to the left of the peak $A^1$, in the line of the X-ray diffraction pattern when viewed along the intensity axis perpendicular to the 2θ axis, and $B^2$ is in a corresponding manner the nearest pronounced minimum to the right of the peak $A^1$ and $C^1$ is the point at which a straight line drawn from the peak $A^1$ perpendicular to the 2θ axis intersects a straight line connecting the points $B^1$ and $B^2$, then the intensity of the reflection 1 is the length of the linear segment $A^1C^1$ which extends from the peak $A^1$ to the point $C^1$. The expression minimum means a point at which the slope of a tangent to the curve in a base region of the reflection 1 changes from a negative value to a positive value, or a point at which the slope tends to zero, the coordinates of the 2θ axis and of the intensity axis being used for specifying the slope.

In this document, the half-width is correspondingly the length of the linear segment between the two intersection points $H^1$ and $H^2$ if a line parallel to the 2θ axis is drawn in the middle of the linear segment $A^1C^1$, where $H^1$ and $H^2$ are in each case the first intersection point of this parallel line with the above-defined line of the X-ray diffraction pattern to the left and right of $A^1$.

An exemplary procedure for determining half-width and intensity is also shown in FIG. 6 in DE-A 10046672.

In addition to the reflections h, i and k, the X-ray diffraction pattern of multimetal oxide active materials (I) to be used according to the invention advantageously also contains, as a rule, further reflections whose peaks are at the following diffraction angles (2θ):

9.0±0.4° (l), 6.7±0.4° (o) and 7.9±0.4° (p).

It is advantageous if the X-ray diffraction pattern of the catalytically active oxide materials of the formula (I) additionally contains a reflection whose peak is at the following diffraction angle (2θ):

45.2±0.4° (q).

Frequently, the X-ray diffraction pattern of multimetal oxide active materials (I) also contains the reflections 29.2±0.4° (m) and 35.4±0.4° (n).

If the catalytically active oxide material of the formula (I) contains the k-phase, its X-ray diffraction pattern generally also contains reflections whose peaks are at the following diffraction angles (2θ):

36.2±0.4° and 50.0±0.4°.

If the reflection h is assigned the intensity 100, it is advantageous according to the invention if the reflections i, l, m, n, o, p and q have the following intensities on the same intensity scale:

i: from 5 to 95, frequently from 5 to 80, in some cases from 10 to 60;

l: from 1 to 30;

m: from 1 to 40;

n: from 1 to 40;

o: from 1 to 30;

p: from 1 to 30 and q: from 5 to 60.

If the X-ray diffraction pattern contains reflections from among the abovementioned additional reflections, the half-width thereof is as a rule ≦1°.

All data in this document which relate to an X-ray diffraction pattern are based on an X-ray diffraction pattern produced using Cu—Kα radiation (Siemens diffractometer Theta-Theta D-5000, tube voltage: 40 kV, tube current: 40 mA, aperture V20 (variable), collimator aperture V20 (variable), secondary monochromator aperture (0.1 mm), detector aperture (0.6 mm), measuring interval (2θ): 0.02°, measuring time per step: 2.4 s, detector: scintillation counter).

The specific surface area of multimetal oxide active materials (I) to be used according to the invention is often from 1 to 30 m²/g (BET surface area, nitrogen).

Otherwise, the novel process can be carried out as described in JP-A 7-53448.

This means that a single reaction zone is sufficient for carrying out the novel process. In this reaction zone, exclusively multimetal oxide active materials of the formula (I), i.e. multimetal oxide active materials of a single type, are present as catalytically active materials.

This is unusual since heterogeneously catalyzed gas-phase oxidation of propene to acrylic acid takes place very generally in two successive steps. In the first step, propene is usually substantially oxidized to acrolein and, in the second step, acrolein formed in the first step is usually oxidized to acrylic acid.

Conventional processes for heterogeneously catalyzed gas-phase oxidation of propene to acrylic acid therefore usually use a specific catalyst type tailored to the oxidation step for each of the two abovementioned oxidation steps.

This means that the conventional processes for the heterogeneously catalyzed gas-phase oxidation of propene to acrylic acid operate with two reaction zones, in contrast to the novel process.

In the novel process, only one or more than one multimetal oxide active material having the stoichiometry I can of course be present in the one reaction zone A. Of course, the catalysts to be employed according to the invention can be diluted with the inert material as also recommended as support material in this document.

In the novel process, only one heating medium temperature or a heating medium temperature changing along the reaction zone A may prevail along the one reaction zone A for heating the reaction zone A. This temperature change may be increasing or decreasing.

If the novel process is carried out in the form of a fixed-bed oxidation, it is expediently carried out in a tube-bundle reactor whose catalyst tubes are loaded with the catalyst. Usually, a liquid, as a rule a salt bath, is passed around the catalyst tube as a heating medium.

A plurality of temperature zones along the reaction zone A can then be realized in a simple manner by passing more than one salt bath around the catalyst tubes in sections along the catalyst tube.

Considered over the reactor, the reaction gas mixture is fed in the catalyst tubes either cocurrently or countercurrently to the salt bath. The salt bath itself can flow parallel to the catalyst tubes. However, a transverse flow can of course also be superposed on this parallel flow. In general, the salt bath can also flow in a meandering manner around the catalyst tube, which meandering flow, considered over the reactor, is cocurrent or countercurrent to the reaction gas mixture.

In the novel process, the reaction temperature along the entire reaction zone A may be from 200 to 500° C. Usually, it is from 250 to 450° C. Preferably, the reaction temperature is from 330 to 420° C., particularly preferably from 350 to 400° C.

In the novel process, the operating pressure may be either 1 atm, less than 1 atm or more than 1 atm. According to the invention, typical operating pressures are from 1.5 to 10, frequently from 1.5 to 4, bar The propene to be used for the novel process does not have to meet any particularly high requirements with respect to its purity.

For example, propene (also referred to as crude propene) of the two specifications below can be used completely without problems as propene for the novel process, as for all one- or two-stage processes for the heterogeneously catalyzed gas-phase oxidation of propene to acrolein and/or acrylic acid very generally:

a) Polymer-grade propylene:

| | |
|---|---|
| ≧99.6% by weight | Propene, |
| ≧0.4% by weight | Propane, |
| ≦300 ppm by weight | Ethane and/or methane, |
| ≦5 ppm by weight | $C_4$-hydrocarbons, |
| ≦1 ppm by weight | Acetylene, |
| ≦7 ppm by weight | Ethylene, |
| ≦5 ppm by weight | Water, |
| ≦2 ppm by weight | $O_2$, |
| ≦2 ppm by weight | Sulfur-containing compounds (calculated as sulfur), |
| ≦1 ppm by weight | Chlorine-containing compounds (calculated as chlorine), |
| ≦5 ppm by weight | $CO_2$, |
| ≦5 ppm by weight | CO, |
| ≦10 ppm by weight | Cyclopropane, |
| ≦5 ppm by weight | Propadiene and/or propyne, |
| ≦10 ppm by weight | $C_{\geq 5}$-hydrocarbons and |
| ≦10 ppm by weight | Carbonyl-containing compounds (calculated as $Ni(CO)_4$). | b) Chemical-grade propylene:

| | |
|---|---|
| ≧94% by weight | Propene, |
| ≦6% by weight | Propane, |
| ≦0.2% by weight | Methane and/or ethane, |
| ≦5 ppm by weight | Ethylene, |
| ≦1 ppm by weight | Acetylene, |
| ≦20 ppm by weight | Propadiene and/or propyne, |
| ≦100 ppm by weight | Cyclopropane, |
| ≦50 ppm by weight | Butene, |
| ≦50 ppm by weight | Butadiene, |
| ≦200 ppm by weight | $C_4$-hydrocarbons, |
| ≦10 ppm by weight | $C_{\geq 5}$-hydrocarbons, |
| ≦2 ppm by weight | Sulfur-containing compounds (calculated as sulfur), |
| ≦0.1 ppm by weight | Sulfides (calculated as $H_2S$), |
| ≦1 ppm by weight | Chlorine-containing compounds (calculated as chlorine), |
| ≦0.1 ppm by weight | Chlorides (calculated as $Cl^{\ominus}$) and |
| ≦30 ppm by weight | Water. |

Of course, all abovementioned possible impurities of the propene can however each also be present in from two to ten times the stated individual amount in the crude propene without adversely affecting the usability of the crude propene for the novel process or for the known processes for the one- or two-stage heterogeneously catalyzed gas-phase oxidation of propene to acrolein and/or acrylic acid very generally.

This is true particularly when the saturated hydrocarbons, the steam, the oxides of carbon or the molecular oxygen are in any case compounds which participate in the reaction in the abovementioned processes either as inert diluent gases or as reactants in large amounts. Usually, the crude propene as such is used as a mixture with recycle gas, air and/or molecular oxygen and/or dilute air and/or inert gas for the novel process and all other processes for the heterogeneously catalyzed gas-phase oxidation of propene to acrolein and/or acrylic acid.

However, another suitable propene source for the novel process is propene which is formed as a byproduct in a process differing from the novel process. This propene may be accompanied by other impurities which essentially present no problems in the novel process.

Both pure oxygen and air or air enriched with oxygen or depleted in oxygen may be used as an oxygen source for the novel process.

In addition to molecular oxygen and propene, a reaction gas starting mixture to be used for the novel process usually also contains at least one diluent gas. Nitrogen, oxides of carbon, noble gases and lower hydrocarbons, such as methane, ethane and propane, are suitable as such a diluent gas. Frequently, steam is also used as a diluent gas. Mixtures of abovementioned gases often form the diluent gas for the novel process.

It is advantageous according to the invention if the novel heterogeneously catalyzed oxidation of the propene is carried out in the presence of propane.

Typically, the reaction gas starting mixture for the novel process has the following composition (molar ratios):

Propene:oxygen:$H_2O$:other diluent gases=1:(0.1–10):(0–70):(0–20).

Preferably, the abovementioned ratio is 1:(1–5):(1–40):(0–10).

If propane is used as the diluent gas, some of it may likewise be oxidized to acrylic acid in the novel process.

It is advantageous according to the invention if the reaction gas starting mixture contains molecular nitrogen, CO, $CO_2$, steam and propane as diluent gas.

The molar propane:propene ratio in the novel process may assume the following values: from 0 to 15, frequently from 0 to 10, often from 0 to 5, expediently from 0.01 to 3.

In the novel process, the catalyst space velocity with respect to propene may be, for example, from 80 to 250 l (S.T.P.)/l·h. The space velocity with respect to reaction gas starting mixture is frequently from 3 000 to 15 000, often from 1 000 to 10 000, l (S.T.P.)/l·h.

Of course, a product gas mixture which does not consist exclusively of acrylic acid is obtained in the novel process. Rather, in addition to unconverted propene, the product gas mixture contains secondary components, such as propane, acrolein, $CO_2$, CO, $H_2O$, acetic acid, propionic acid, etc., from which the acrylic acid has to be separated.

This can be effected as generally known from the heterogeneously catalyzed two-stage gas-phase oxidation (carried out in two reaction zones) of propene to acrylic acid.

This means that the acrylic acid present can be taken up from the product gas mixture by absorption with water or by absorption with a high-boiling inert hydrophobic organic solvent (for example a mixture of diphenyl ether and diphyl, which, if required, may also contain additives, such as dimethyl phthalate). The resulting mixture of absorbent and acrylic acid can then be worked up in a manner known per se by rectification, extraction and/or crystallization to give pure acrylic acid. Alternatively, the basic separation of the acrylic acid from the product gas mixture can also be effected by fractional condensation, as described, for example, in DE-A 19 924 532.

The resulting aqueous acrylic acid condensate can then be further purified, for example by fractional crystallization (e.g. suspension crystallization and/or layer crystallization).

The residual gas mixture remaining in the basic isolation of acrylic acid contains in particular unconverted propene. This can be separated from the residual gas mixture, for example, by fractional rectification under pressure and then recycled to the novel gas-phase oxidation. However, it is more advantageous to bring the residual gas into contact with a hydrophobic organic solvent which is preferably capable of absorbing the propene (for example by passing said solvent through) in an extraction apparatus.

The absorbed propene can be liberated again by subsequent desorption and/or stripping with air and can be recycled to the novel process. In this way, economical total propene conversions can be achieved. If propene is oxidized in the presence of propane, propene and propane are preferably separated off together and recycled.

A noteworthy feature of the novel process is that it permits both high propene conversions and high selectivities in the acrylic acid formation in only one reaction zone with a single pass of the reaction gas mixture.

The multimetal oxide active materials (I) to be used according to the invention can of course also be employed in the novel process in a form diluted with finely divided, for example colloidal, materials, such as silica, titanium dioxide, alumina, zirconium oxide or niobium oxide.

The dilution mass ratio may be up to 9 (diluent):1 (active material), i.e. possible dilution mass ratios are, for example, 6 (diluent):1 (active material) and 3 (diluent):1 (active material). The diluent may be incorporated before and/or after the calcination. If the incorporation is effected before the calcination, the diluent must be chosen so that it is substantially retained as such during the calcination. This is generally true, for example, in the case of oxides calcined at correspondingly high temperatures.

The multimetal oxide active materials (I) to be used according to the invention are also suitable for the gas-phase catalytic oxidation of acrolein and of propane to acrylic acid and of methacrolein and other $C_4$ precursors, e.g. n-butane or isobutane, to methacrylic acid. They are of course also suitable for the gas-phase catalytic ammoxidation of propene and/or propane to acrylonitrile. The catalysts consumed in the novel process can be regenerated several times by loading with oxygen-containing gases, e.g. air or air depleted in oxygen or enriched with oxygen, to which steam may also have been added, at temperatures $\leq$ reaction temperature.

EXAMPLES

A) Preparation of Catalysts a) According to the Invention 1. 706.2 g of ammonium heptamolybdate hydrate having an $MoO_3$ content of 81.53% by weight (ideal composition: $(NH_4)_6Mo_7O_{24} \cdot 4H_2O$, from Starck) were dissolved, while stirring, in 6 000 ml of water which was at 80° C. First 141.0 g of ammonium metavanadate ($V_2O_5$ content of 77.4% by weight, ideal composition: $NH_4VO_3$, from G. f. E. Nürnberg) and then 211.28 g of telluric acid (99% by weight of $H_6TeO_6$, from Fluka) were added in succession, with further stirring, to the resulting clear colorless solution while maintaining the 80° C. A solution A was obtained. The solution A was allowed to cool to 30° C. An aqueous niobium oxalate solution, consisting of 221.28 g of niobium oxalate (from H.C. Starck, DE-Goslar, Nb content=20.1% by weight) and 2 000 ml of water at 30° C., was added to the clear, red solution A cooled to 30° C., with further stirring and while maintaining the 30° C.

The mixture obtained was dried in a spray drier (apparatus from Niro, DE, $T^{in}$=350° C., $T^{out}$=105° C.). 150 g of the resulting solids were heated from 25° C. to 275° C. at a heating rate of 5° C./min under air (10 l/h) in a rotary sphere oven according to FIG. 1 (quartz glass sphere having an internal volume of 1 liter; 1=oven housing, 2=rotating flask, 3=heated space, 4=nitrogen/air stream). Immediately thereafter, heating was effected from 275° C. to 650° C. at a heating rate of 2° C./min under a molecular nitrogen stream (10 l (S.T.P.)/h) and the solid was kept at this temperature under the nitrogen stream for 6 hours. It was then cooled to 25° C. by leaving it to stand, while maintaining the nitrogen stream. A black calcination product was obtained.

230 g of black calcination product thus produced were added to 2 300 g of a 20% strength by weight aqueous HNO$_3$ (nitric acid). The resulting aqueous suspension was stirred at 70° C. for 7 hours. It was then cooled to 25° C. The solid present in the black suspension was separated from the aqueous phase by filtration, washed nitrate-free with water and then dried overnight in a through-circulation drying oven at 120° C. Of the 230 g used, 181.4 g (=78.7% by weight) of solid a) remained after the treatment described above.

Figure 2:
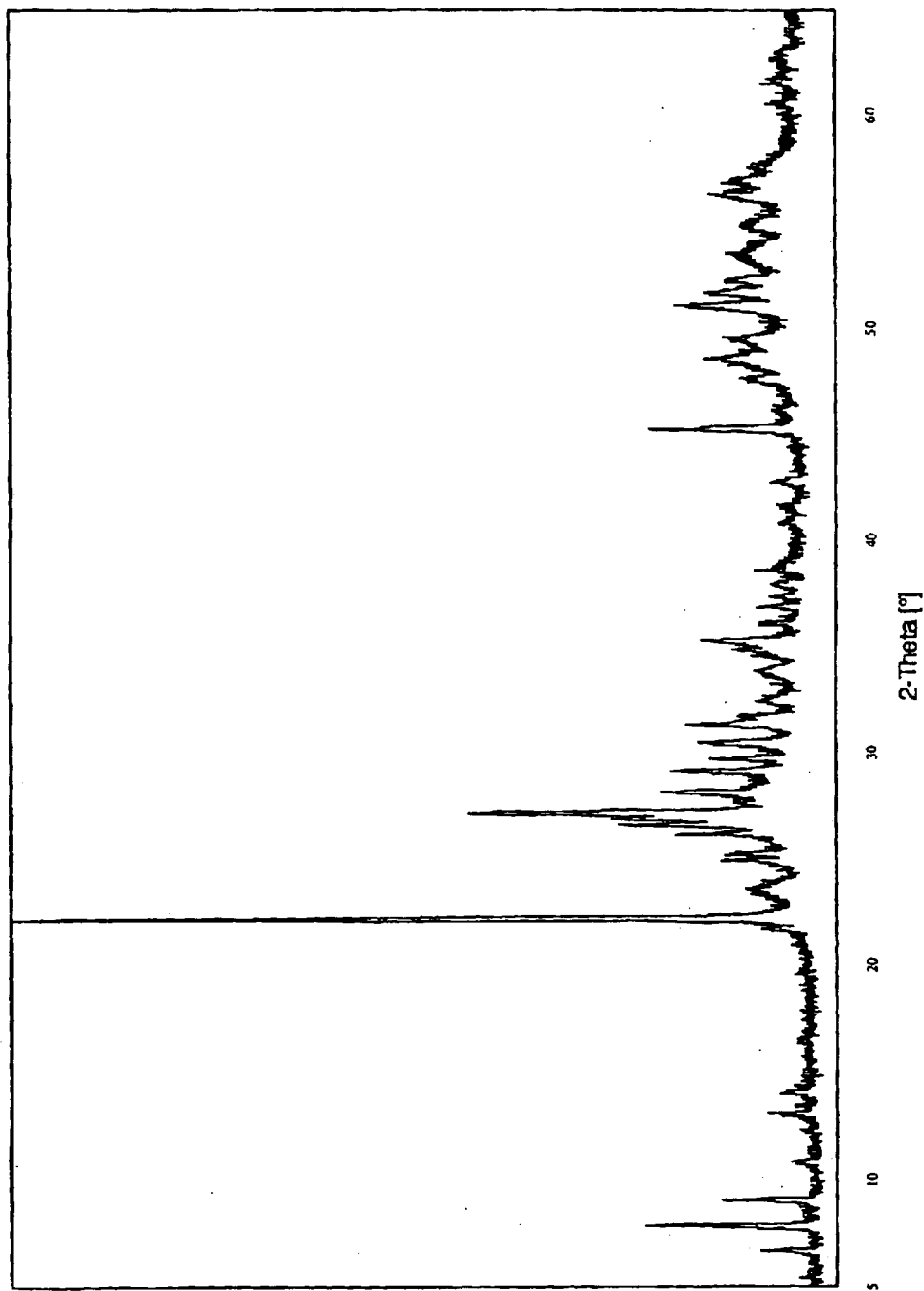
FIG. 2 is the X-ray diffraction pattern of multimetal oxide catalyst of Example (Sa)

85 g of the solid a) obtained were introduced, together with 150 ml of water, into a milling apparatus comprising ZrO$_2$ (consisting of a 500 ml ZrO$_2$ beaker and 200 ml of ZrO$_2$ grinding media having an external diameter of 2 mm) and milled in a PM 4000 high-speed planetary mill from Retsch, 42759 Haan, Germany, at a speed of 300 revolutions per minute for 30 minutes. The resulting content of the milling beaker was separated from the ZrO$_2$ grinding media by means of a sieve. The solids content of the suspension obtained was separated off by means of filtration (in a paper filter) and then dried overnight at 120° C. in through-circulation drying oven. The chemical composition of the resulting powder (particle size$\leq$0.12 mm) was Mo$_1$V$_{0.15}$Te$_{0.09}$Nb$_{0.16}$O$_x$. The associated X-ray diffraction pattern is shown in FIG. 2 (R=0.76). It shows exclusively i-phase. 75 g of the resulting powder were applied to 162 g of spherical supports having a diameter of 2.2–3.2 mm (R$_z$=45 μm, support material=steatite from Ceramtec, Germany, total pore volume of the support$\leq$1% by volume, based on the total support volume).

For this purpose, the support was initially taken in a coating drum having an internal volume of 2 l (angle of inclination of the central axis of the drum relative to the horizontal=30$_5$). The drum was rotated at 25 revolutions per minute. About 30 ml of a mixture of glycerol and water (glycerol:water weight ratio=1:3) was sprayed onto the support over 60 minutes via an atomizer nozzle operated with 300 l (S.T.P.)/h compressed air. The nozzle was installed in such a way that the spray cone wet the supports conveyed in the drum by metal driver plates to the uppermost point of the inclined drum, in the upper half of the rolling path. The finely divided active material powder was introduced into the drum via a powder screw, the point of addition of the powder being inside the rolling path or below the spray cone. By periodic repetition of wetting and powder metering, the support provided with a base coat itself became the support in the subsequent period.

After the end of the coating, the coated support was dried for 16 hours at 120° C. in a through-circulation drying oven (from Binder, Germany, internal volume 53 l). Glycerol was removed by a subsequent 2-hour heat treatment at 150° C. under air. A coated catalyst S$_a$ to be used according to the invention was obtained.

b) According to the Invention

Figure 3:
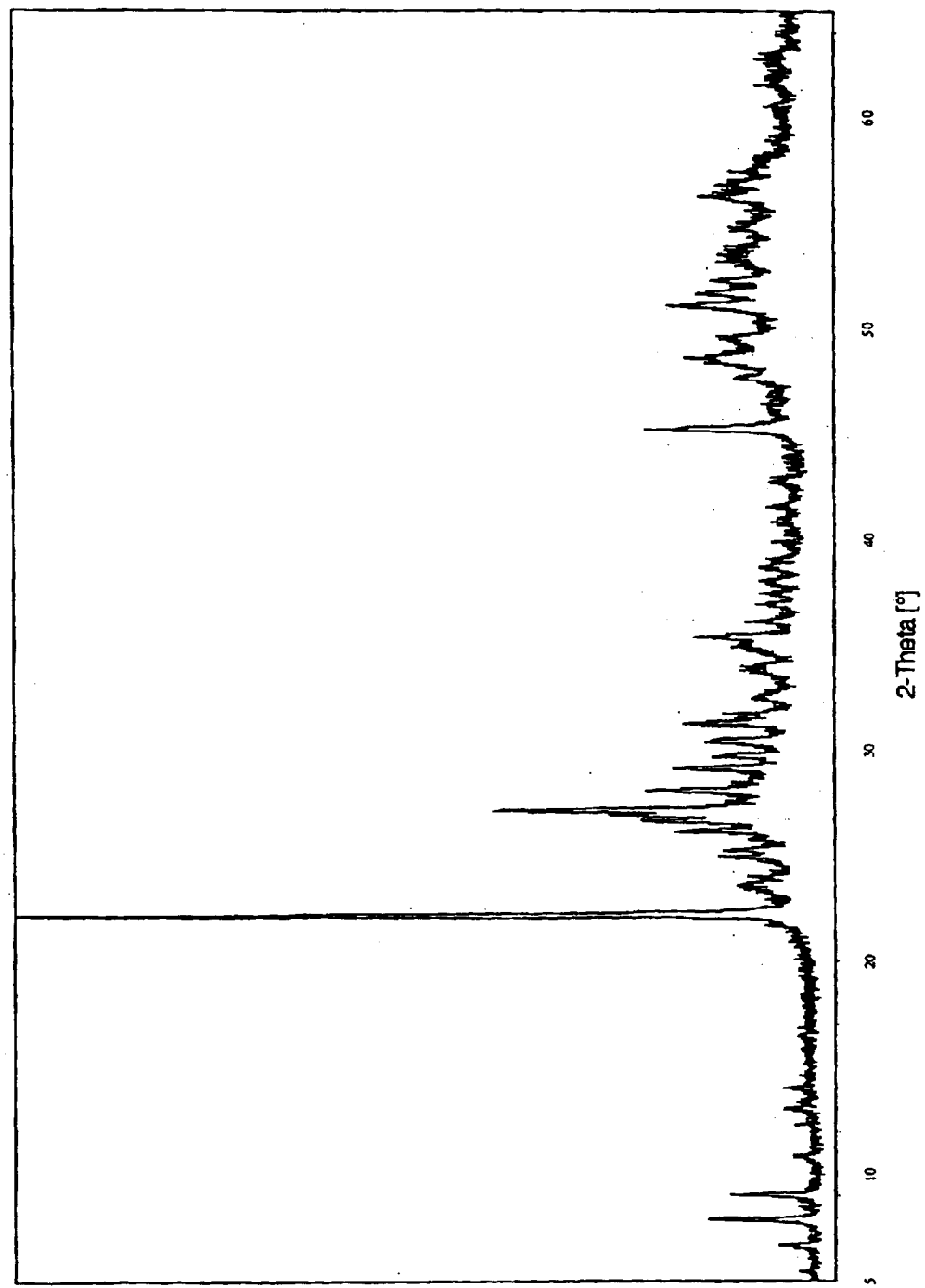
FIG. 3 is the X-ray diffraction pattern of multimetal oxide catalyst of Example (Sb)
Figure 4:
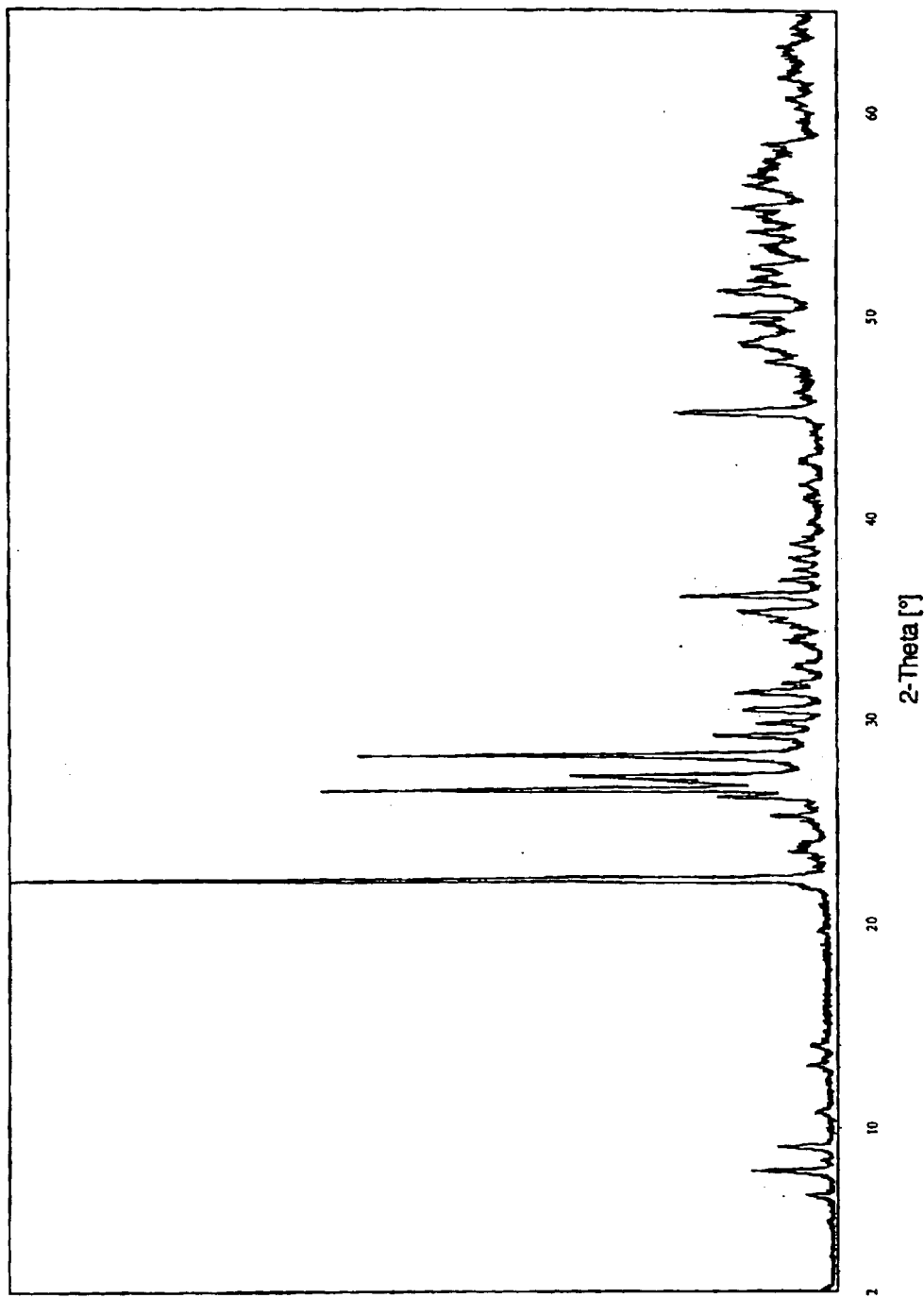
FIG. 4 is the X-ray diffraction pattern of multimetal oxide comparison catalyst of Example (Sc)

A solid a) was prepared as under a). 85 g of the solid a) obtained were milled as in a). Instead of 150 ml of water, however, 150 ml of a 7.5% strength by weight aqueous HNO$_3$ solution were used. After the separation of the ZrO2 grinding media over a sieve, the solids content of the suspension obtained was separated off by means of filtration (paper filter), washed nitrate-free with water and then dried overnight at 120° C. in a through-circulation drying oven. The chemical composition of the resulting powder (particle size$\leq$0.12 mm) was Mo$_1$V$_{0.15}$Te$_{0.088}$Nb$_{0.16}$O$_x$. The associated X-ray diffraction pattern is shown in FIG. 3 (R=0.74). It shows exclusively i-phase. A coated catalyst S$_b$ to be used according to the invention was prepared as in a) using 75 g of the resulting powder.

c) Comparison 1 287.25 g of ammonium metavandate (V$_2$O$_5$ content of 77.4% by weight, ideal composition: NH$_4$VO$_3$, from G. f. E. Nürnberg) were dissolved in 44.6 l of water in a stainless steel container at 80° C. The resulting clear yellowish solution was cooled to 60° C. Thereafter, 1 683.75 g of telluric acid (99% by weight of H$_6$TeO$_6$, from Fluka) and 5 868.0 g of ammonium heptamolybdate hydrate having a MoO content of 81.53% by weight (ideal composition: (NH$_4$)$_6$Mo$_7$O$_{24}$·4H$_2$O, from Starck) were added in succession to this solution while maintaining the 60° C. and with stirring. The resulting deep red solution A was cooled was cooled to 30° C. Separately therefrom, 1 559.0 g of ammonium niobium oxalate (21.1% by weight of Nb from Starck/Goslar) were dissolved in 8.3 l of water at 60° C. in a second stainless steel container. The resulting solution B to 30° C. The solutions A and B were combined at 30° C., the solution B being stirred into the solution A. The addition was effected over a period of 3 minutes. An orange-red suspension formed. This suspension was then spray-dried (spray tower from Nipolosa; the temperature of the receiver was kept at 30° C., T$^{in}$=240° C., T$^{out}$=110° C.; duration of drying: 1.5 hours). The resulting spray-dried powder was likewise orange. After admixing 2%, based on the weight of the powder, of finely divided graphite (from Timcal, Switzerland), the powder was tableted to give rings having the geometry 16 mm×8 mm×2.5 mm (external diameter× internal diameter×height), and the resulting lateral compressive strength was 11 N. 100 g of these rings were calcined in a rotary sphere oven according to FIG. 1. For this purpose, first heating was effected linearly from 25° C. to 275° C. in the course of 35 minutes under an air stream of 50 l (S.T.P.)/h and this temperature was maintained for 1 hour while maintaining the air stream. Thereafter, the air stream was replaced by a nitrogen stream of 50 l (S.T.P.)/h and heating was effected linearly from 275° C. to 600° C. in the course of 25 minutes. This temperature and the nitrogen stream were maintained for 2 hours. Finally, cooling was effected to 25° C. by leaving to stand while maintaining the nitrogen stream. The calcined material was then milled in a Retsch mill (centrifugal mill, type ZM 100, from Retsch, Germany) (particle size$\leq$0.12 mm). A black powder having the chemical composition Mo$_{1.0}$V$_{0.33}$Te$_{0.15}$Nb$_{0.11}$O$_x$ resulted. The associated X-ray diffraction pattern is shown in FIG. 4 (R=0.35). It shows a mixture of i-phase and k-phase. The i-phase fraction is 65% by weight. A comparative coated catalyst S$_c$ was prepared as in a) using 75 g of the powder.

d) Comparison 128.0 g of ammonium metavanadate (V$_2$O$_5$ content of 77.4% by weight, ideal composition: NH$_4$VO$_3$, from G. f. E. Nürnberg) were dissolved in 2 925 ml of water in a stainless steel container at 80° C. The resulting yellowish clear solution was cooled to 60° C. Thereafter, 304.5 g of telluric acid (99% by weight of H$_6$TeO$_6$, from Fluka) and 585.0 g of ammonium heptamolybdate (81.53% by weight of MoO$_3$, from Starck, ideal composition: (NH$_4$)$_6$Mo$_7$O$_{24}$·4H$_2$O) were added in succession to this solution while maintaining the 60° C. and with stirring. The resulting deep red solution A was cooled to 30° C. Separately therefrom, 69.6 g of niobic acid (Nb content 48.6% by weight, from Starck), together with 343.5 g of oxalic acid dihydrate, were dissolved in 750 ml of water at 60° C. in a second stainless steel container. The resulting solution B was cooled to 30° C. The solutions A and B were combined at 30° C., the solution B being stirred into the solution A. The addition was effected over a period of 3 minutes. An orange-red suspension formed. This suspension was then spray-dried (spray tower from Nipolosa; the temperature of the receiver was kept at 30° C., $T^{in}$=330° C., $T^{out}$=110° C.; duration of drying: 2 h). The resulting spray-dried material was a homogeneous powder having an olive-green color.

100 g of the spray-dried powder were calcined in a rotary sphere oven according to FIG. 1. For this purpose, first heating was effected linearly from 25° C. to 275° C. in the course of 27.5 minutes under an air stream of 50 l (S.T.P.)/h and this temperature was maintained for 1 hour while maintaining the air stream. Thereafter, the air stream was replaced by a nitrogen stream of 50 l (S.T.P.)/h and heating was effected linearly for from 275° C. to 600° C. in the course of 32.5 minutes. This temperature and the nitrogen stream were maintained for 2 hours. Finally, cooling to 25° C. was effected by leaving to stand while maintaining the nitrogen stream. The calcined material was then milled in a Retsch mill (centrifugal mill, type ZM 100, from Retsch, Germany) (particle size≦0.12 mm). A black powder having the chemical composition $Mo_{1.0}V_{0.33}Te_{0.41}Nb_{0.11}O_x$ resulted. The associated X-ray diffraction pattern is shown in FIG. 5 (R=0). It shows substantially pure k-phase. A comparative coated catalyst $S_d$ was prepared as in a) using 75 g of the powder.

B) Testing of the Catalysts a) A V2A stainless steel reaction tube (length=120 cm, external diameter=21 mm, internal diameter=15 mm) was loaded in each case with the coated catalysts from A). The loading length was chosen as 70 cm. A 30 cm long preliminary bed of steatite balls (diameter: 2.2–3.2 mm, from Ceramtec), which may also be dispensed with, served for warming up the reaction gas starting mixture. The reaction tube after the catalyst zone was finally filled with the same steatite balls (this may also be dispensed with). The reaction tube was heated over its entire length by means of a salt bath at 370° C. flowing around it. The reaction gas starting mixture used was a mixture of 5% by volume of propene, 9.5% by volume of oxygen and 85.5% by volume of nitrogen. The loading of the reaction tube with reaction gas starting mixture was 100 l (S.T.P.)/h in all cases. In the product gas stream, the selectivity S of the acrylic acid formation in the case of a single pass through the reaction tube was determined by gas chromatographic analysis. Table 1 below shows the propene conversions (C) and the selectivity S of the acrylic acid formation, obtained using the various coated catalysts.

TABLE 1

| Coated catalyst | C [mol %] | S [mol %] |
|---|---|---|
| $S_a$ | 78.3 | 66.2 |
| $S_b$ | 75.5 | 62.6 |
| $S_d$ | 25 | 68 |

Omission of the inert beds does not impair the results.

b) 35 g of various coated catalysts from A) were installed in a tubular reactor (length 140 cm, internal diameter 8.5 mm, external diameter 60 mm, catalyst bed length 52 cm; additionally, for warming up the reaction gas starting mixture, 30 cm long preliminary bed of steatite balls from Ceramtec (2.2–3.2 mm diameter); furthermore, the reaction tube was finally filled with the same steatite beads after the catalyst zone) which was heated by electrical heating mats. At a mat temperature of 350° C., a residence time (based on catalyst bed) of 2.4 s and a pressure of 2 bar absolute, the results listed in table 2 were obtained using a feed (reaction gas starting mixture) having the molar composition propene:air:water=3.3:50:46.7, depending on the coated catalyst used.

TABLE 2

| Coated catalyst | C [mol %] | S [mol %] |
|---|---|---|
| $S_a$ | 97 | 71 |
| $S_c$ | 69 | 71 |
| $S_d$ | 25 | 72 |

When a feed having the molar composition propane:propene:air:water—0.5:0.5:15:14 was used, C with $S_a$ was 57 mol % and the S obtained was 71 mol %.

We claim:

1. A process, comprising:

preparing acrylic acid by heterogeneously oxidizing propene to acrylic acid in the gas phase with molecular oxygen over at least one multimetal oxide catalyst material present in a reaction zone, wherein the multimetal oxide catalyst material has a stoichiometry I $$Mo_1V_bM_c^1M_d^2O_n \tag{I},$$

where $M_1$ is Te and/or Sb, $M_2$ is at least one element from the group consisting of Nb, Ta, W, Ti, Al, Zr, Cr, Mn, Ga, Fe, Ru, Co, Rh, Ni, Pd, Pt, La, Bi, B, Ce, Sn, Zn, Si and In, b is from 0.01 to 1, c is from >0 to 1, d is from >0 to 1 and n is a number which is determined by the valency and frequency of the elements other than oxygen in (I), wherein the X-ray diffraction pattern of the at least one multimetal oxide active material (I) has reflections h, i and k whose peaks are at the diffraction angles (2θ) 22.2±0.4° (h), 27.3±0.4° (i) and 28.2±0.4° (k), the reflection h being the one with the strongest intensity within the X-ray diffraction pattern and having a half-width of not more than 0.5°, the intensity $P_i$ of the reflection i and the intensity $P_k$ of the reflection k fulfills the relationship 0.65≦R≦0.85, where R is the intensity ratio defined by the formula $$R=P_i/(P_i+P_k)$$

and the half-width of the reflection i and that of the reflection k are each ≦1°.

2. The process as claimed in claim 1, wherein 0.67≦R≦0.75.

3. The process as claimed in claim 1, wherein R ranges from 0.70 to 0.75.

4. The process as claimed in claim 1, wherein $M^1$ is Te.

5. The process as claimed in claim 1, wherein $M^2$ is Nb.

6. The process as claimed in claim 1, wherein b ranges from 0.1 to 0.6.

7. The process as claimed in claim 1, wherein c ranges from 0.05 to 0.4.

8. The process as claimed in claim 1, wherein d ranges from 0.1 to 0.6.

9. The process as claimed in claim 1, wherein the X-ray diffraction pattern has no reflection at the peak position 2θ=50.0±0.03°.

10. The process as claimed in claim 1, wherein the propene is oxidized in the presence of propane.

11. The process as claimed in claim 1, wherein, in the gas phase of the reaction, the mole ratio of propene:oxygen water:other diluent gases is 1:(0.1–10):(0–70):(0–20).

12. The process as claimed in claim 11, wherein, in the gas phase of the reaction, the mole ratio of propene:oxygen water:other diluent gases is 1:(1–5):(1–40):(0–10).

13. The process as claimed in claim 1, wherein the catalyst space velocity ranges from 80 to 250 liters (STP)/l·hr.

14. The process as claimed in claim 1, wherein the space velocity of the starting propene containing gas ranges from 3,000 to 15,000 liters (STP)/l·hr.

15. The process as claimed in claim 14, wherein said space velocity ranges from 1,000 to 10,000 liters (STP)/l·hr.

16. The process as claimed in claim 1, wherein the temperature of the reaction ranges from 200 to 500° C.

17. The process as claimed in claim 16, wherein the temperature of the reaction ranges from 250 to 450° C.

18. The process as claimed in claim 1, wherein the pressure of the reaction ranges from 1.5 to 10 bar.

19. The process as claimed in claim 1, wherein, with the presence of k phase material in the catalyst, the X-ray pattern of the multimetal oxide material further comprises reflections having peaks at diffraction angle 2θ of:

36.2±0.4° and 50.0±0.4°.

* * * * *

UNITED STATES PATENT AND TRADEMARK OFFICE
CERTIFICATE OF CORRECTION

PATENT NO. : 7,026,506 B2  Page 1 of 1
APPLICATION NO. : 10/474202
DATED : April 11, 2006
INVENTOR(S) : Borgmeier et al.

It is certified that error appears in the above-identified patent and that said Letters Patent is hereby corrected as shown below:

On the title page, the Terminal Disclaimer information has been omitted. Item (45) and the Notice information should read as follows:

--[45] **Date of Patent: *Apr. 11, 2006**

[* ] Notice: Subject to any disclaimer, the term of this patent is extended or adjusted under 35 U.S.C. 154(b) by 90 days.

This patent is subject to an terminal disclaimer.--

Signed and Sealed this

Fifteenth Day of August, 2006

JON W. DUDAS
*Director of the United States Patent and Trademark Office*